United States Patent [19]
Weippert

[11] Patent Number: 5,817,256
[45] Date of Patent: Oct. 6, 1998

[54] IMMERSION OIL

[75] Inventor: Hans-Joachim Weippert, Aalen, Germany

[73] Assignee: Carl-Zeiss-Stiftung, Heidenheim, Germany

[21] Appl. No.: 811,236

[22] Filed: Mar. 3, 1997

[30] Foreign Application Priority Data

Mar. 2, 1996 [DE] Germany .................. 196 08 081.9

[51] Int. Cl.$^6$ .............................. F21V 9/00; C07C 69/34; C09K 31/02
[52] U.S. Cl. .............................. 252/582; 252/1; 252/589; 560/194
[58] Field of Search ............................ 560/194; 252/582, 252/589, 1

[56] References Cited

U.S. PATENT DOCUMENTS 2,814,639 11/1957 Bartlett et al. .

4,789,490 12/1988 Tanaka ................................ 252/582

FOREIGN PATENT DOCUMENTS 0209621 1/1987 European Pat. Off. .

*Primary Examiner*—Philip Tucker
*Attorney, Agent, or Firm*—Walter Ottesen

[57] ABSTRACT

The invention is directed to an immersion oil for microscopy. The immersion oil includes an ester or ether with tricyclodecane structure as a main constituent and one or more high-boiling liquids as minor constituents. The immersion oil is free of halogens and exhibits a high UV-transmissibility and is characterized by low intrinsic fluorescence because the components utilized can be vacuum distilled.

20 Claims, 2 Drawing Sheets

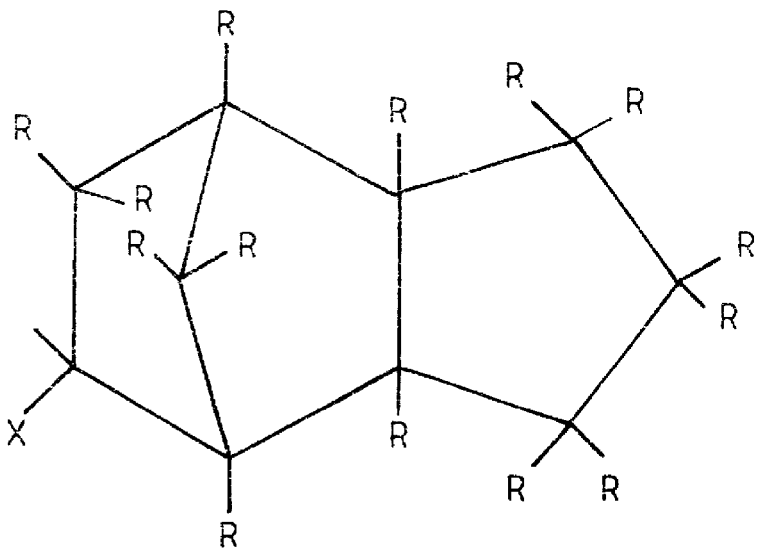
FIG. 1a
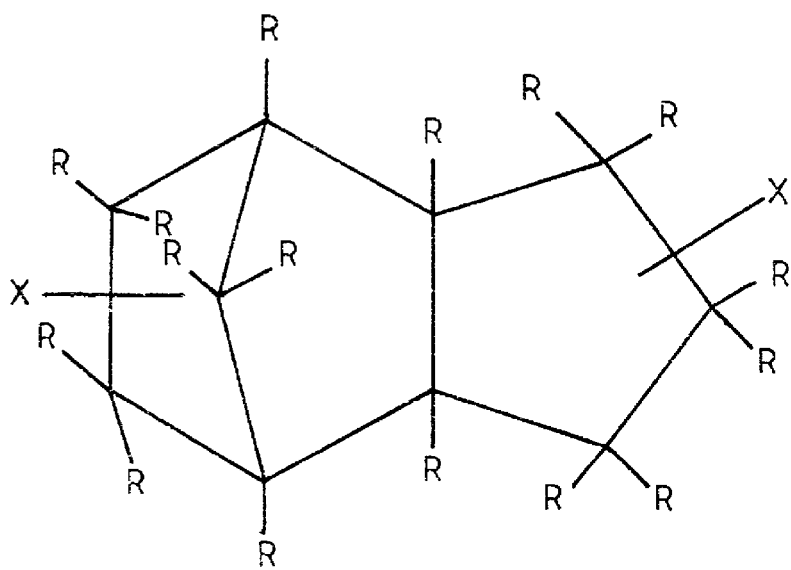
FIG. 1b
FIG. 1c
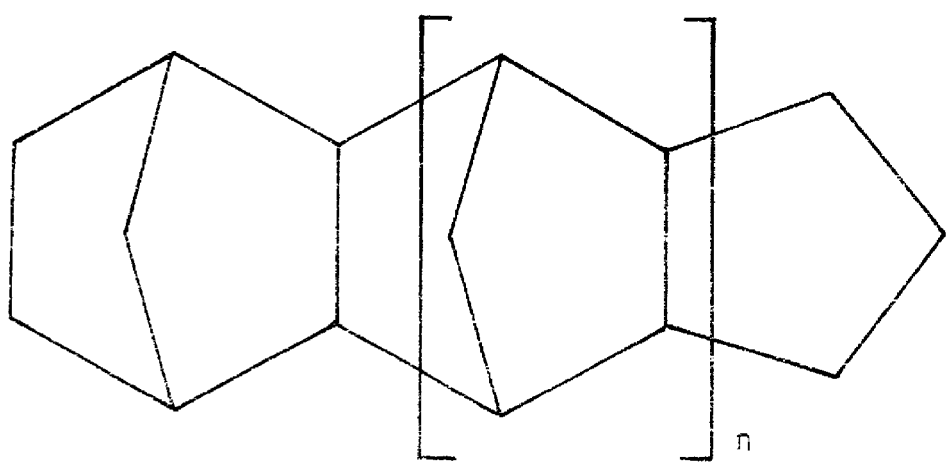

IMMERSION OIL

BACKGROUND OF THE INVENTION

A substantial portion of the immersion oils offered today which have a refractive index of greater than 1.5 include chlorinated paraffin as a main constituent. Chlorinated paraffins are, however, considered to be a dangerous working substance and furthermore exhibit a poor environmental compatibility.

Halogen-free immersion oils are available in addition to immersion oils on the basis of chlorinated paraffin. The main problem in the manufacture of halogen-free immersion oils is the unfavorable relationship of the refractive index and dispersion for most of the halogen-free liquids having refractive indices having a value of greater than 1.5. The Abbe number, which describes the dispersion, deviates in such immersion oils often significantly from the range specified for DIN 58884 for the Abbe number of 44±5 (DIN) and the range ISO 8036/1 for the Abbe number 44±3 (ISO). Known halogen-free immersion oils, which have an Abbe number greater than 41, are either unsatisfactory with respect to their UV-transmissibility or exhibit an intrinsic fluorescence which is too great. Halogen-free immersion oils having values for the Abbe number in the upper tolerance range of the above-mentioned two standards (that is, with an Abbe number $v_e > 45$) are not known.

European patent publication 0,209,621 discloses, in addition to halogen-containing immersion oils, also embodiments for halogen-free immersion oils. Two embodiments for halogen-free immersion oils contain tricyclodecanol as a minor constituent. With respect to the UV-transmissibility (for wavelengths below 400 nm) no information is provided by this patent publication. Furthermore, the viscosity has values of 1,000 and 2000 mm²/s at 25° C. is too great for most applications, that is, the use thereof can very easily cause air bubbles to become included.

SUMMARY OF THE INVENTION

It is an object of the invention to provide a base substance for the production of immersion oils for microscopy with which immersion oils having Abbe numbers between 40 and 50 can be produced while also having low intrinsic fluorescence and high UVA-transmissibility and being free of halogen.

The immersion oil of the invention is for microscopy and includes: as a main constituent, the tricyclodecane derivative or derivatives of substances having the basic structure of the tricyclodecane.

The immersion oil of the invention includes, as main constituents, tricyclodecane derivatives or derivatives of substances having base structures of the tricyclodecanes. The portion of the tricyclodecane derivative and/or the derivative of substances having base structures of tricyclodecanes has at least 50% by weight of the total immersion oil in the embodiments wherein the immersion oil is a two-substance mixture and at least 40% by weight for those embodiments wherein the immersion oil is a three-substance or multi-substance mixture. The immersion oil can also contain several tricyclodecane derivatives. In such cases, the sum of all tricyclodecane derivatives have at least 40% by weight of the immersion oil.

The invention proceeds from the recognition that tricyclodecane derivatives or derivatives of substance having the base structure of the tricyclodecanes exhibit a relatively high refractive index while at the same time having a high Abbe number and are therefore superbly suitable as a main component for the immersion oil. The relatively high refractive index while at the same time providing a high Abbe number is because of the ring structure of the tricyclodecanes (TCD). An immersion oil containing a TCD-derivative or derivative of substances having TCD base structure as a main constituent can therefore be free of halogen.

The derivatives of tricyclodecane as well as the substances with tricyclodecane base structures are preferably ester compounds or ether compounds. Here, esters and ethers of tricyclodecane as well as of tricyclodecane-oligomers and tricyclodecane-polymers can be considered. Also, one or several hydrogens of tricyclodecane skeletons can be substituted by other organic residues in addition to the esters and ethers of monomers, oligomers and polymers of tricyclodecanes.

In the preferred embodiments, the main constituents of the immersion oils comprise tricyclodecanemethylolester or tricyclodecanemethylolether as these liquids can be vacuum distilled because of their molecular structure and therefore provide a high degree of purity. Immersion oils having minimum intrinsic fluorescence can be produced from tricyclodecanemethylol esters and tricyclodecanemethylol ethers. The production of immersion oils to the standard values for the refractive index takes place simply by mixing the TCD methylolesters or the TCD methylolethers with suitable high boiling liquids such as softeners, paraffin oils, polypropylene glycols, et cetera.

For the production of TCD-esters and TCD-ethers, the readily available TCD-alcohols, namely, TCD-alcohol M (=8(9)-hydroxymethyltricyclo[$5.2.1.0^{2,6}$]decane) and TCD alcohol DM (=3(4), 8(9)-dihydroxymethyltricyclo[$5.2.1.0^{2,6}$]decane) which are available from Hoechst AG, Frankfurt, Germany. The tricyclodecanemethylolesters or di-(tricyclodecanemethylol)esters can be synthesized via esterification of these alcohols with dicarboxylic acids such as phthalic acid, isophthalic acid, terephthalic acid, malonic acid, succinic acid, malic acid, glutaric acid, adipic acid or sebacic acid in accordance with conventional esterification methods.

Di-(TCD-methylol)adipate has been shown to be especially suitable as a main constituent for immersion oils. Here, the percent by weight of the di-(TCD-methylol) adipate is at least 60%. As further components for adjusting the refractive index, butylbenzylphthalate and/or di-(propyleneglycol-1,2)dibenzoate can, for example, be added. The di-(TCD-methylol)adipate is likewise odorless as the other di-(TCD-methylol)ester in contrast to tricyclodecane alcohols and has no significant irritation with respect to human skin.

DESCRIPTION OF THE PREFERRED EMBODIMENTS OF THE INVENTION

There are many substances having the base structure of the tricyclodecanes whose ester derivatives or ether derivatives can be considered for the immersion oil of the invention. The structure formulas of such substances are shown in FIGS. 1a to 1c. The substances shown can be a TCD-monomer (FIGS. 1a and 1b) or a TCD-oligomer or a TCD-polymer (see FIG. 1c) for which the ring structure repeatedly occurs n-times. The ring structure is enclosed by brackets in FIG. 1c. One or several hydrogen atoms of the TCD-skeleton can, furthermore, and as shown in FIGS. 1a and 1b, be substituted by a residual R. Examples of suitable residuals R are presented in Table III. The substitution of the hydrogen by residual R has only a subordinate influence on the physical characteristics which are important for immersion oils.

The starting point for the ester synthesis can be TCD-alcohols (wherein X identifies an alcohol residual, preferably OH or $CH_2OH$) or TCD carboxylic acids (wherein X identifies a carboxylic acid residual, preferably $(COOH)_2$. Examples of TCD-alcohols known in the literature are presented in Table IV. Here, TCD-monoalcohols, TCD-dialcohols as well as TCD-trialcohols can be used. The TCD-alcohol DM (dialcohol) and the TCD-alcohol M (monoalcohol) are, however, preferred because of their large-scale availability. The corresponding TCD-esters can be produced by converting the TCD-alcohols with a carboxylic acid in accordance with conventional synthesis methods. Suitable monocarboxylic acids, dicarboxylic acids or tricarboxylic acids are presented in Table V. The subsequent purification of the TCD-esters takes place with vacuum or high vacuum distillation. The temperature stability and the high boiling point of the di-(tricyclodecanemethylol)ester (boiling point over 200° C. at a pressure of $10^{-5}$ mbar) is of special significance. From this, excellent vacuum distillation results.

One can proceed from TCD-carboxylic acids as an alternative to ester synthesis from TCD-alcohols. Suitable TCD-monocarboxylic acids and TCD-dicarboxylic acids known from the literature are presented in Table VI. In this case, the esterification takes place by conversion with a monofunctional or a higher alcohol. Suitable alcohols are presented in Table VII.

In the same manner as with the synthesis of the TCD-esters, the corresponding ethers can be produced via conversion of the TCD-monoalcohols in accordance with conventional ether synthesis methods. The TCD-monoalcohols are presented in Table IV.

Figure 2:
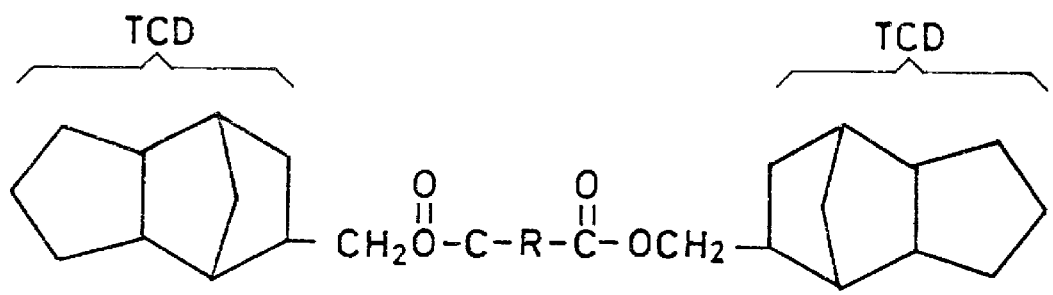
In FIG. 2, the structure of di-(TCD-methylol)esters in general are shown and, in FIG. 3, the structures of di-(TCD-methylol)adipate are shown. The TCD-groups can themselves have the structures shown in FIGS. 1a to 1c with the residuals R presented in Table III.
Figure 3:
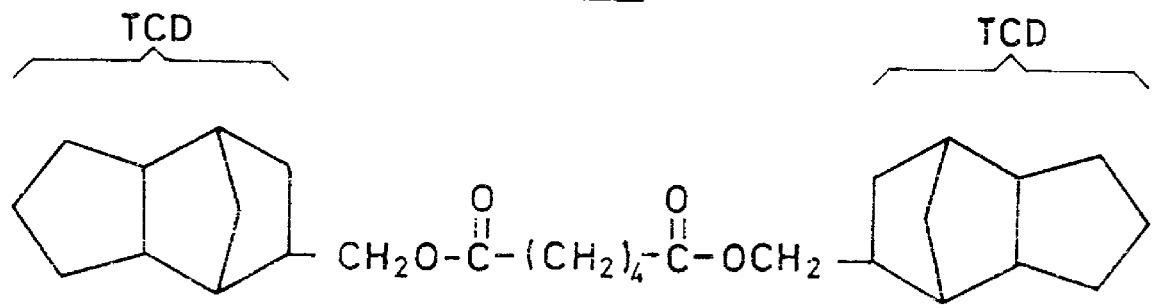

The physical characteristics of several preferred di-(TCD-methylol)esters are presented in Table Ia with the characteristics being important for the immersion oils. The refractive index $n_e>1.5$ and the simultaneously high Abbe number $v_e>=46$ ($v_e=47$ for the di-(TCD-methylol)malinate) and even Abbe numbers $v_e>50$ for the other given di-(TCD-methylol)esters are essential for the superb suitability of aliphatic di-(TCD-methylol)esters as the main constituent of immersion oils. Furthermore, the excellent UV-transmissibility of the di-(TCD-methylol)esters is significant. This excellent UV-transmissibility is only for wavelengths under 320 nm for a 10 mm layer thickness at less than 10% transmission.

Table Ib shows a comparison of the physical characteristics of an immersion oil of the invention and known halogen-containing and halogen-free immersion oils. The composition of the immersion oil of the invention is presented under number 11 in Table II.

In Table II, the compositions and the physical characteristics of 14 preferred mixtures of a di-(TCD-methylol)ester and one or several high-boiling liquids is presented. The percent by weight of the di-(TCD-methylol)ester for the two component mixtures is between 68 and 98.5 percent by weight and, for the 3-component mixtures, between 51 and 70 percent by weight. As shown by the numerical values for the Abbe number and for the viscosity, almost any desirable viscosity value between 100 $mm^2/s$ and 6000 $mm^2/s$ for Abbe numbers in the range of 39 to 50 can be adjusted. Mixtures having viscosities in the range of 400 $mm^2/s$ to 600 $mm^2/s$ and therefore the embodiments 6, 11 and 12 are especially preferred for most applications.

In principle, the immersion oil can be put together from several di-(TCD-methylol)esters as a main constituent and several high-boiling liquids as a minor constituent to adjust the refractive index. The starting substances for a low residual fluorescence must be prepared in high purity and the usable quantities are relatively low. For this reason, the two-substance mixture is especially preferred when lower production costs are wanted.

German patent application P 196 08 081.9, filed Mar. 2, 1996, on which the claim of priority herein is based, is incorporated herein by reference.

It is understood that the foregoing description is that of the preferred embodiments of the invention and that various changes and modifications may be made thereto without departing from the spirit and scope of the invention as defined in the appended claims.

TABLE Ia

Physical Characteristics of Di (TCDmethylol)-esters

| Substance | Refractive Indices at 20° C. | | Dispersion (Abbe - No.) $\zeta e$ | Viscosity at 20° C. |
| --- | --- | --- | --- | --- |
| | $n_D$ (589,3 nm) | $n_D$ (546,1 nm) | DIN 58 884 | DIN 51 562 |
| Di-(TCDmethylol)phthalate | 1.5497 | 1.5533 | 39 | ca. 280000 mPa*s |
| Di-(TCDmethylol)malonate | 1.5166 | 1.5191 | 51 | 1900 $mm^2/s$ |
| Di-(TCDmethylol)suoccinate | 1.5149 | 1.5173 | 51 | 1600 $mm^2/s$ |
| Di-(TCDmethylol)glutarate | 1.5137 | 1.5161 | 51 | 1300 $mm^2/s$ |
| Di-(TCDmethylol)adipate | 1.5118 | 1.5142 | 51 | 1100 $mm^2/s$ |
| Di-(TCDmethylol)sebaoate | 1.5057 | 1.5082 | 51 | 800 $mm^2/s$ |
| Di-(TCDmethylol)maleinate | 1.5258 | 1.5284 | 47 | 9000 $mm^2/s$ |
| For Comparison: TCD-Alcohol M | 1.5169 | 105192 | 52 | 1100 mPa*s |

| Substance | Limit of UV - Permeability at d = 10 mm T ≤ 10% | Other Characteristics |
| --- | --- | --- |
| Di-(TCDmethylol)phthalate | at 319 nm | |

TABLE Ia-continued

Physical Characteristics of Di (TCDmethylol)-esters

| | | |
|---|---|---|
| Di-(TCDmethylol)malonate | at 276 nm and Absorption Bands at 302 nm | Boiling Point:180–185° C. at $10^{-5}$ mbar |
| Di-(TCDmethylol)suoccinate | at 287 nm | |
| Di-(TCDmethylol)glutarate | at 286 nm | |
| Di-(TCDmethylol)adipate | at 262 nm | Boiling Point:220–225° C. at $10^{-5}$ mbar |
| | | Pourpoint: −20° C. (ISO 3016) |
| | | Flash Point (COC): 265° C. (ISO 2592) |
| | | Density $D_{20}$ = 1.090 g/cm$^3$ (DIN 51 757) |
| Di-(TCDmethylol)sebaoate | at 260 nm | |
| Di-(TCDmethylol)maleinate | at 317 nm | |
| | | Boiling Point: 226° C. at 1013 mbar |
| For Comparison: | at 238 nm | Pourpoint: −24° C. |
| | | Flash Point (COC): 130° C. |
| TCD-Alcohol M | Density D20 = 1.044g/cm$^3$ | |

TABLE Ib

Physical Data of Immersion Oils

| | CARL ZEISS Immersion Oil 518 C | Cargille Immersion Oil Type A | Cargille Immersion Oil Type B | Cargille Immersion Oil Type DF | Immersion Oil of the Invention according to Tab. II, Nr. 11 |
|---|---|---|---|---|---|
| Chemical Basis | Chlorinated paraffins, Phthalic acid ester | aliphatic Hydrocarbons, Terphenyls, hydrated Terphenyls | aliphatic Hydrocarbons, Terphenyls, hydrated Terphenyls | Chlorinated Paraffins, alkyl-phthalate, Butylbenzyl-phthalate | Di-(TCDmethylol)-adipate Butylbenzyl-phthalate |
| containing halogens | yes | no | no | yes | no |
| $n^{23}_D$ | 1.5151 | 1.5150 | 1.5150 | 1.5152 | 1.5152 |
| $n^{23}_e$ | 1.5180 | 1.5181 | 1.5180 | 1.5183 | 1.5180 |
| Dispersion $\zeta e$ | 43.5 | 41 | 42.5 | 41.5 | 45.5 |
| Kinematic Viscosity at 20° C. (mm$^2$/s) | 460 | 180 | 1700 | 440 | 560 |
| UV-Permeability at d = 10 mm (%) Transmission (against water) | | | | | |
| • at 420 nm | 94 | 86 | 88 | 96.5 | >99 |
| • at 400 nm | 89 | 65 | 78 | 94 | 99 |
| • at 380 nm | 78 | 46 | 60 | 89 | 98 |
| • at 365 nm | 64 | 18 | 37 | 81 | 97 |
| • at 350 nm | 41 | <5 | <5 | 70 | 93 |
| • at 330 nm | <8 | <0.1 | <0.1 | 45 | 85 |
| Residual fluorescence (mg/l quinine sulfate equivalent amount) | | | | | |
| • F 365/450 nm | 0.15–0.25 | 0.42 | 0.40 | 0.21 | 0.020 |
| • F 405/485 nm | 4.5–6.5 | 140 | 140 | 5.8 | 0.65 |

TABLE II

Embodiments for halogen-free Immersion Oils

| Example | Components | Weight portions (Wt-%) | Refractive indices at 23° C. $n_D$ (589.3 nm) | $n_e$ (546.1 nm) | Dispersion (Abbe-No.) $\zeta e$ | Viscosity at 20° C. (mm$^2$/s) |
|---|---|---|---|---|---|---|
| 1 | Di-(TCDmethylol)phthalate | 7.0 | | | | |
| | Polypropyleneglycol (1,2) 400 | 30 | 1.5150 | 1.5181 | 40 | 6000 |
| 2 | Di-(TCDmethylol)phthalate | 58 | | | | |
| | Dioctylphthalate | 42 | 1.5150 | 1.5182 | 39 | 960 |

TABLE II-continued

Embodiments for halogen-free Immersion Oils

| Example | Components | Weight portions (Wt-%) | Refractive indices at 23° C. $n_D$ (589.3 nm) | $n_e$ (546.1 nm) | Dispersion (Abbe-No.) $\zeta e$ | Viscosity at 20° C. (mm²/s) |
|---|---|---|---|---|---|---|
| 3 | Di-(TCDmethylol)malonate | 98.5 | | | | |
| | Paraffin oil | 1.5 | 1.5150 | 1.5176 | 50 | 1400 |
| 4 | Di-(TCDmethylol)malonate | 97.5 | | | | |
| | Dioctylphthalate | 2.5 | 1.5150 | 1.5176 | 50 | 1350 |
| 5 | Di-(TCDmethylol)succinate | 88.5 | | | | |
| | Butylbenzylphthalate | 11.5 | 1.5150 | 1.5177 | 48 | 810 |
| 6 | Di-(TCDmethylol)succinate | 70 | | | | |
| | Butylbenzylphthalate | 24.5 | 1.5150 | 1.5179 | 44 | 440 |
| | Dioctylsebacate | 5.5 | | | | |
| 7 | Di-(TCDmethylol)succinate | 66.5 | | | | |
| | Dibenzylether | 22.0 | 1.5150 | 1.5180 | 42 | 100 |
| | Dioctylsebacate | 11.5 | | | | |
| 8 | Di-(TCDmethylol)maleinate | 84 | | | | |
| | Paraffin oil | 16 | 1.5150 | 1.5178 | 48 | 2500 |
| 9 | Di-(TCDmethylol)maleinate | 89.5 | | | | |
| | Dioctylsebacate | 10.5 | 1.150 | 1.5178 | 47 | 1800 |
| 10 | Di-(TCDmethylol)glutarate | 90 | | | | |
| | Butylbenzylphthalate | 10 | 1.5150 | 1.5177 | 49 | 820 |
| 11 | Di-(TCDmethylol)adipate | 83 | | | | |
| | Butylbenzylphthalate | 17 | 1.5150 | 1.5178 | 45 | 560 |
| 12 | Di-(TCDmethylol)adipate | 71.5 | | | | |
| | Di-(propyleneglycol-1,2)dibenzoate | 28.5 | 1.5150 | 1.5179 | 43 | 510 |
| 13 | Di-(TCDmethylol)sebacate | 68 | | | | |
| | Butylbenzylphthalate | 32 | 1.5150 | 1.5180 | 42 | 300 |

TABLE III

Organic Groups (FIGS. 1a and 1b)

$X = -CH_2OH, -COOH$ $R = -H, -CH_3, -C_2H_5, -C_3H_7, -C_4H_9, -C_5H_{11},$ $-C_6H_{13}, -C_7H_{15}, -C_8H_{17}, -C_9H_{19}, -C_{10}H_{21}$ $-CH_2-CH=CH_2, -CH=CH_2, -CH=CH-CH_3,$ $-CH_2-CH=CH-CH_3, -OH$ $-OCH_3, -OC_2H_5, -OC_3H_7, -OC_4H_9,$ $-OC_5H_{11}, -OC_6H_{13}$

[cyclic structures: cyclobutyl, cyclopentyl, cyclohexyl, bicyclic decalin-type, dicyclopentadienyl-type structures]

TABLE III-continued

Organic Groups (FIGS. 1a and 1b)

[aromatic structures: methylphenyl, ethylphenyl, methoxyphenyl, ethoxyphenyl, methylnaphthyl, and $-CH_2-$ linked cyclobutyl, cyclopentyl, cyclohexyl, bicyclic groups, and $-OCH_2-$ linked bicyclic groups]

TABLE III-continued
Organic Groups (FIGS. 1a and 1b)
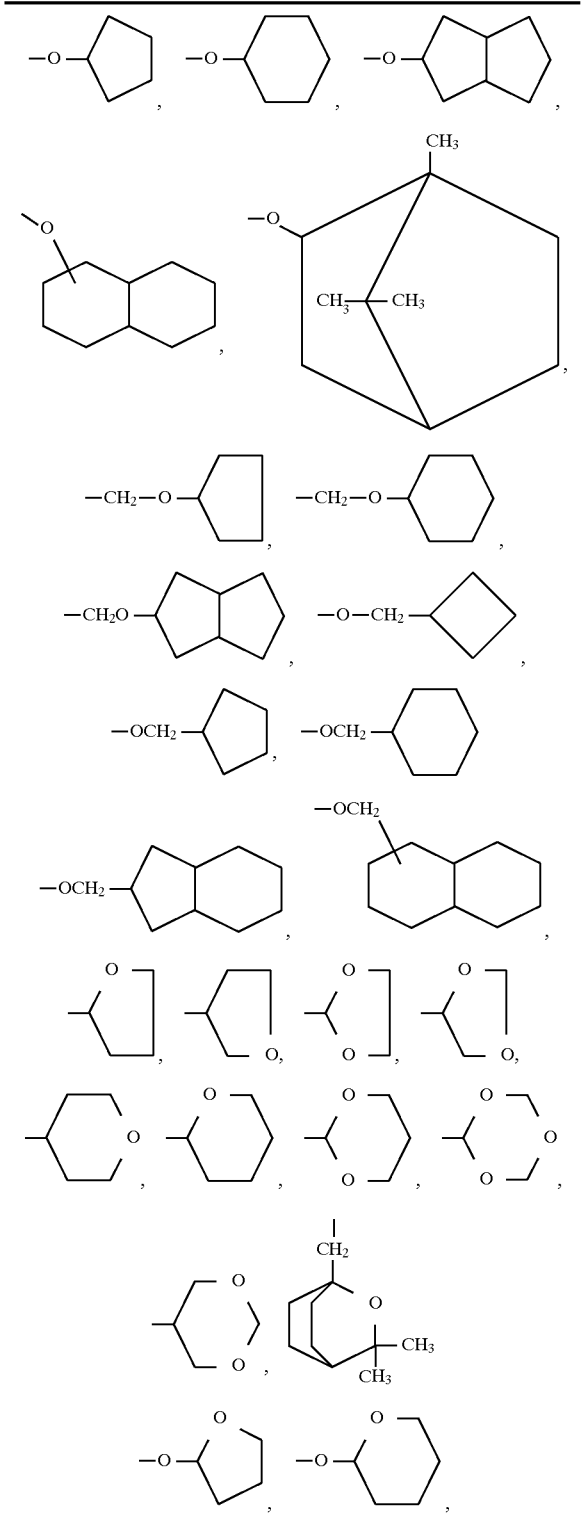
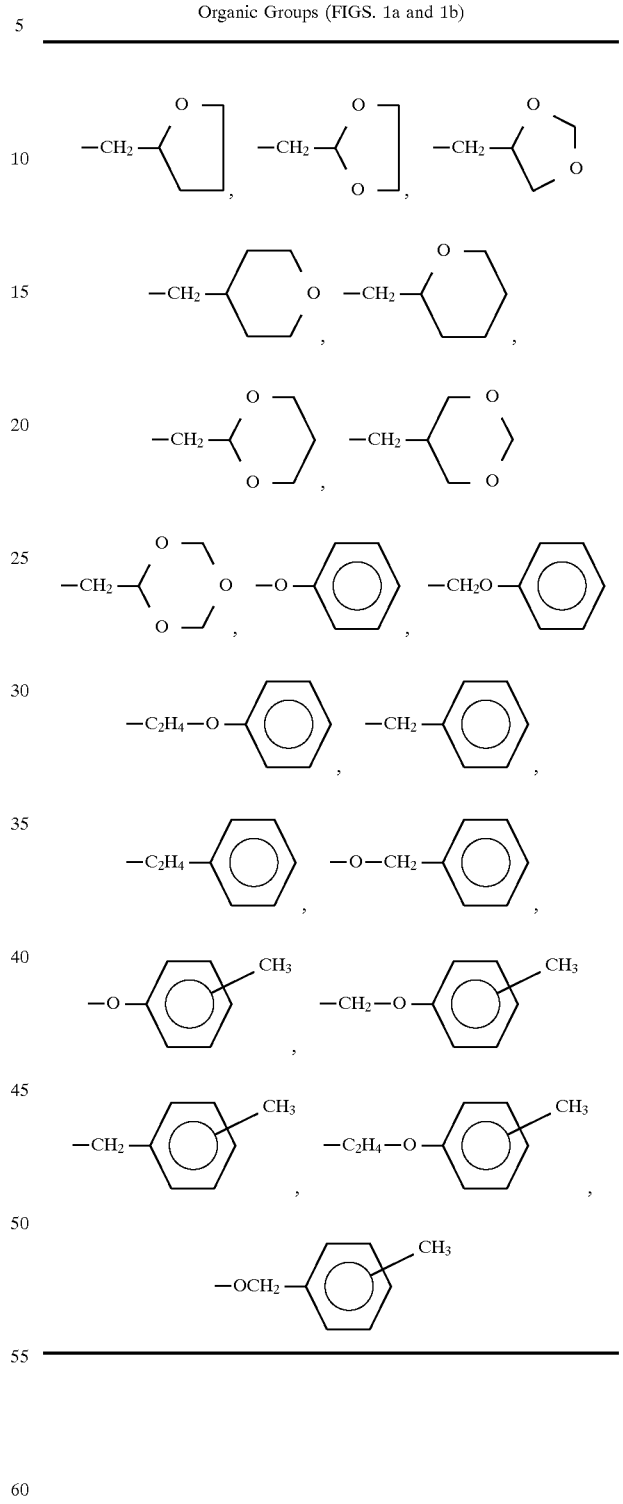

TABLE IV

TCD - Alcohols

TCD-(Mono)alcohols:

I. 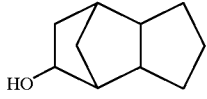

TCD-Alcohol = 8-Hydroxy-tricyclo [5.2.1.0$^{2,6}$]decane

II. 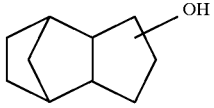

3(4)-Hydroxy-tricyclo[5.2.1.0$^{2,6}$]decane

```
         R—COOH
                  → Monoester
         ┌─COOH
         R
         └─COOH
                  → Diester
              COOH
              │                TCD - Ester
    HOOC—R—COOH
                  → Triester
         ┌─OH
         R
         └─OH, COCl$_2$
                  → Polyol - Carbonate
                    (Carbonic acid ester)
```

III. 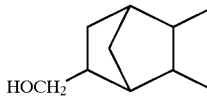

TCD-Alcohol M = 8-Hydroxymethyl-tricyclo[5.2.1.0$^{2,6}$]decane

IV. 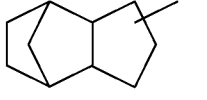

3(4)Hydroxymethyl-tricyclo[5.2.1.0$^{2,6}$]decane

V. 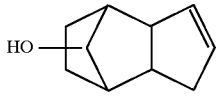

TCD-Alcohol E = 8(9)-Hydroxy-tricyclo[5.2.1.0$^{2,6}$]dec-3-ene

VI. 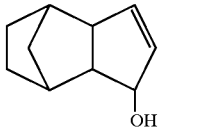

5-Hydroxy-tricyclo[5.2.1.0$^{2,6}$]dec-3-ene

TCD-Di-Alcohols:

VII. 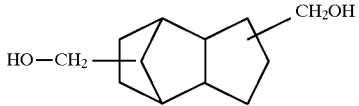

TCD-Alcohol DM = 3(4), 8(9)-Bis(hydroxymethyl)tricyclo[5.2.1.0$^{2,6}$]decane

```
   R$_1$—COOH
              ┐
              │
              │  TCD - Ester
              │
   R$_2$—COOH
              ┘
   R$_1$ = R$_2$
   or
   R$_1$ ≠ R$_2$
```

TABLE IV-continued

TCD - Alcohols

VIII. 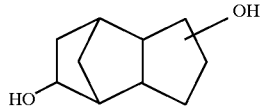

3(4), 8(9)-Bis(hydroxy)tricyclo[5.2.1.0$^{2,6}$]decane

IX. 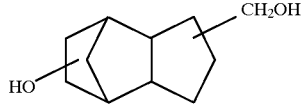

TCD-Alcohol OM = 8 Hydroxy-4(5)hydroxymethyl-tricyclo[5.2.1.0$^{2,6}$]decane

X. 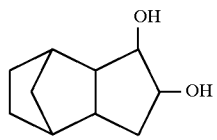

3.4-Dihydroxy-tricyclo[5.2.1.0$^{2,6}$]decane

XI. 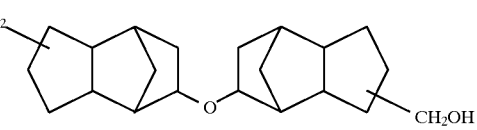

Di-(TCD-Alcohol M)ether = Di(tricyclo[5.2.1.0$^{2,6}$]decyl-8,8'-ether-3(4),

XII. 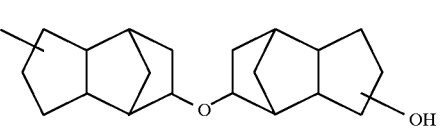

Di-(TCD-Alcohol A)ether = Di(tricyclo[5.2.1.0$^{2,6}$]decyl-8,8'-ether-3(4), 3'(4'))diol

TCD - tri-Alcohols

III. 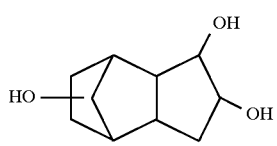 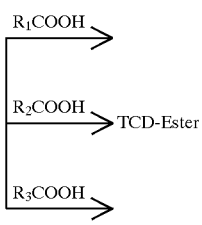

TCD-Alcohol TO =
8(9), 3,4-Tri-hydroxy-tricyclo[5.2.1.0$^{2,6}$]decane $R_1$ = $R_2$ = $R_3$
or
$R_1 \neq R_2$ = $R_3$
$R_1$ = $R_2 \neq R_3$
$R_1 \neq R_2 \neq R_3$ XIV. 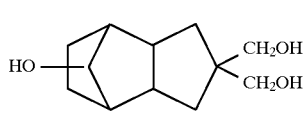

8-Hydroxy-4,4-dihydroxymethyl-tricyclo[5.2.1.0$^{2,6}$]decane

TABLE V

TCD - Carboxylic acids

TCD-(Mono)Carboxylic acids:

XV. 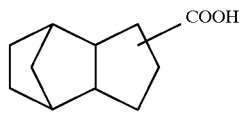

TCD-Carboxylic acid S
Tricyclo[5.2.1.0$^{2,6}$]decane-3(4)carboxylic acid

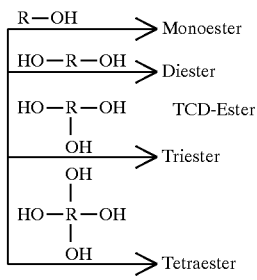

XVI. 

Tricyclo[5.2.1.0$^{2,6}$]decane-8(9)carboxylic acid

XVII. 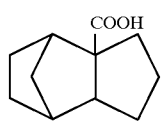

Tricyclo[5.2.1.0$^{2,6}$]decane-2-carboxylic acid

XVIII. 

8-Hydroxy-tricyclo[5.2.1.0$^{2,6}$]decane-3(4)carboxylic acid

TCD-Dicarboxylic Acids:

XIX. 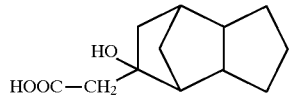

8-Hydroxy-tricyclo[5.2.1.0$^{2,6}$]decane-8-methyl-carboxylic acid

XX. 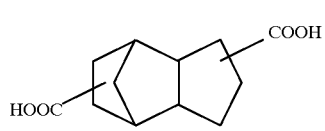

TCD-Carboxylic acid =
Tricyclo[5.2.1.0$^{2,6}$]decane-3(4), 8(9)-dicarboxylic acid $R_1$—OH
TCD-Ester
$R_2$—OH $R_1 = R_2$
or
$R_1 \neq R_2$ XXI. 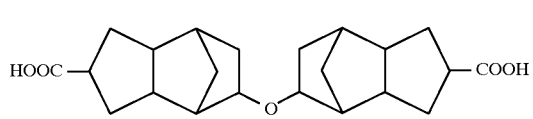

8,8'-Di-(tricyclo[5.2.1.0$^{2,6}$]decyl)ether-4,4'-dicarboxylic acid

---

Literature Sources

B.Cornils, R. Payer: Derivate des Dicyclopentadiens— aktuelle Schlüsselverbindungen Chemiker—Zeitung 98 70–76 (1974)

O. Roelen, K. Büchner et. al., Ruhrchemie Ag, Oberhausen: DBP 934 889 (1955) Verfahren zur Herstellung von Estern und bzw. oder Polyestern der Tricyclodekanreihe.

O. Roelen, K. Büchner et. al., Ruhrchemie AG, Oberhausen: DAS 1036 849 (1956) Verfahren zur Herstellung von als Schmiermittel, Weichmacher oder Polyester geeigneten Estern des Di-(tricyclo-[5.2.1.0$^{2,6}$]decyl)-8,8'äther4,4'-dimethylols, bzw. der Di-(tricyclo-[5.2.1.0$^{2,6}$]decyl-)-8, 8'-äther4,4'-dicarbonsäure.

J. Bartlett, R. Brodkey et. al.: U.S. Pat. No. 2,814,639 (1957) Dimethylol—Tricyclodecanol Esters and Process.

British Petroleum Co. Ltd. Brit. Pat. 847 592 (1960) New Polyesters and their method of preparation.

TABLE VI

Carboxylic Acid for the Synthesis of TCD - Esters

Monocarboxylic Acids:

formic acid
acetic acid
propionic acid
n/isobutyric acid
n/iso-valeric acid
hexanoic acid
heptanoic acid
octanoic acid
nonanoic acid
decanoic acid
undecanoic acid
dodecanoic acid
pivalic acid 2-methylbutyric acid
3-methylbutyric acid
2,2-dimethylbutyric acid
3,3-dimethylbutyric acid
tertiary butyl acetic acid
2-ethyl butyric acid
2-methyl valeric acid
3-methyl valeric acid
4-methyl valeric acid
2,2-dimethyl valeric acid
2-propyl valeric acid
2-methyl hexanoic acid
2-ethyl hexanoic acid
Di-(n-propyl-)acetic acid
crotonic acid
vinylacetic acid
2-methyl crotonic acid
3,3-dimethyl acrylic acid
(3-methyl crotonic acid)
2-pentene acid
4-pentene acid
2-methyl-2-pentene acid
1-adamantane acetic acid
3-cyclohexene-1-carboxylic acid
4-cycloheptene-1 -carboxylic acid
4-cyclooctene-1-carboxylic acid
1 -cycloundecene-1-carboxylic acid
exo-bicyclo[2.2.1]hept-5-ene-2carboxylic acid
(exo-5-Norbornene-2-carboxylic acid)
5-norbornene-2-acrylic acid
3-camphor carboxylic acid
2-cyclopentene-1yl-acetic acid
2,2,3,3-tetramethylcyclopropane carboxylic acid
4-acetylbutyric acid
3-methyl-2-oxovaleric acid
4-methyl-2-oxovaleric acid
5-acetylvaleric acid
2-oxopentanoic acid
2-oxohexanoic acid
7-oxooctanoic acid
5-oxodecanoic acid
7-oxodecanoic acid
2-ethylhexoxy acetic acid
3,6-dioxa heptanoic acid
3,6,9-trioxa decanoic acid
3-methoxycyclohexanoic carboxylic acid 4-methoxycyclohexanoic carboxylic acid
phenyl acetic acid
2-phenyl propionic acid
3-phenylpropionic acid
benzoic acid
2(3,4)-methylbenzoic acid
(toluic acid)

2,2-dimethyl-4-pentene acid
2-hexene acid
3-hexene acid
2-heptene acid
6-heptene acid
2-octene acid
4-ethyl-2-octene acid
2-nonene acid
2-decene acid
ethoxy acetic acid
3-ethoxy-propionic acid
L-menthoxy-acetic acid
cyclopropanecarboxylic acid
2-methylcyclopropane carboxylic acid
cyclobutane carboxylic acid
cyclopentane carboxylic acid
cyclohexane carboxylic acid
cycloheptane carboxylic acid
cyclooctane carboxylic acid
cycloundecanoic carboxylic acid
cyclopentyl acetic acid
cyctohexyl acetic acid
3-cyclopentyl propionic acid
tetrahydrofurane-2-carboxylic acid
tetrahydrofurane-3-carboxylic acid
2-tetrahydroxyfurane acetic acid
1 (2,3,4) methyl-1-cyclohexane carboxylic acid
4-cyclohexyl butyric acid
2-cyclohexyl butyric acid
(α-[ethyl]cyclohexane acetic acid)
2-norborane acetic acid
tricyclo[5.2.1.0$^{2,6}$]decane-2carboxylic acid
tricyclo[5.2.1.0$^{2,6}$]decane-3(4)carboxylic acid
(TCD-acid S)
Tricyclo[5.2.1.0$^{2,6}$]decane8(9)carboxylic acid
Adamantane carboxylic acid
2-phenylcyclopropane-1-carboxylic acid
1 -phenylcyclobutane carboxylic acid
1-phenyl-1 -cyclohexane carboxylic acid
cyclohexylphenyl acetic acid
diphenyl acetic acid
3,3-diphenylpropionic acid
2,2-diphenylpropionic acid
4-phenylvaleric acid
5-phenylvaleric acid
phenoxy acetic acid
3-phenoxypropionic acid
2-phenoxybutyric acid
4-phenoxybutyric acid
11-phenoxyundecanoic acid
3-benzoylpropionic acid
4-benzoylbutyric acid
5-benzoylvaleric acid
2-phenyllevulinic acid
o-toluic acetic acid
m-toluic acetic acid
p-toluic acetic acid
di-p-toluic acetic acid
1-indane carboxylic acid
1,2,3,4-tetrahydro-1(2)-naphthalene carboxylic acid
2-methoxyphenyl acetic acid
3-methoxyphenyl acetic acid
4-methoxyphenyl acetic acid
p-ethoxyphenyl acetic acid
3-(o-methoxyphenyl)propionic acid
3-(p-methoxyphenyl)propionic acid
4-(p-methoxyphenyl)butyric acid

TABLE VI-continued

Carboxylic Acid for the Synthesis of TCD - Esters

2(3,4)biphenylcarboxylic acid
1(2)-naphthalene carboxylic acid
2-phenylbutyric acid
3-phenylbutyric acid
4-phenylbutyric acid
1-phenylcyclopentane carboxylic acid α-cyclopentyl-phenylacetic acid 1-phenyl-1-cyclopropane carboxylic acid 4-ethoxy--3-methoxyphenyl acetic acid
(3,4-dimethOxyphenyl)acetic acid
(2,5-dimethoxyphenyl)acetic acid
3(3,4-dimethoxyphenyl)propionic acid
3,4,5-trimethoxyphenyl acetic acid
1-naphthyl acetic acid
2-naphthyl acetic acid
(2-naphthoxy)acetic acid
2,3-/2,6/3,4/2,4/2,5-dimethylbenzoic acid
2(3,4)-methoxybenzoic acid
2,342,6/3,4/2,4/2,5-dimethoxybenzoic acid
2(2,4)-ethoxybenzoic acid
p-tert.-butyl-benzoic acid
p-n-butoxybenzoic acid
p-cyciohexyloxybenzoic acid
4-acetylbenzoic acid
3-methoxy-4-methyl-benzoic acid
3,4(methylenedioxy)benzoic acid
(piperonylic acid)
3,4,5-trimethoxybenzoic acid
2,4,6-trimethoxybenzoic acid
2,4,5-trimethoxybenzoic acid
2-benzylbenzoic acid
o-phenoxybenzoic acid
2-bibenzylcarboxylic acid
(o-phenethylbenzoic acid)
1-methylindene-2-carboxylic acid
9-fluorene carboxylic acid
xanthene-10-carboxylic acid
dicarboxylic acids:

malonic acid
succinic acid
maleic acid
(toxii acid)
fumaric acid
glutaric acid
glutacon acid
adipic acid
3-hexenediacid (hydromuconic acid)
heptanedioic acid (pimelic acid)
2-ethyl-2-methylsuccinic acid
phenylsuccinic acid
3-methyladipic acid
2,5-dimethyladipic acid
hydroxysuccinic acid
(DL-malic acid)
2-hydroxy-2-isopropylsuccinic acid sulphosuccinic acid
3-hydroxy-3-methylglutaric acid
2,2,5,5-tetramethyladipic acid
2-oxoglutaric acid
(ketoglutaric acid)
2-oxoadipic acid
(α-ketoadipic acid)
3-oxoadipic acid
(β-ketoadipic acid)
4-oxoheptanedioic acid
(4-ketopimelic acid)
acetonedicarboxylic acid
(3-oxoglutaric acid)
3,6-dioxaoctanedioic acid
(3,6-dioxasuberic acid)
3,6,9-trioxaundecanedioic acid
diglycolic acid 1 -m-toluiccyclopentanoic carboxylic acid
1-(p-toluic)-1-cyclopropane carboxylic acid
1-(p-toluic)-1-cyclobutane carboxylic acid
1-(p-toluic)-1-cyclopentane carboxylic acid
1-(p-toluic)-1-cyclohexane carboxylic acid
1-(p-methoxyphenyl)-1-cyclopropane carboxylic acid
1-(p-methoxyphenyl)-1-cyciopentane carboxylic acid
1-(p-methoxyphenyl)-1-cyclohexane carboxylic acid
octanedioic acid
(suberic acid)
nonanedioic acid
(azelaic acid)
decanedioic acid
(sebacic acid)
undecanedioic acid
dodecanedioic acid
tridecanedioic acid
(brassylic acid)
tetradecanedioic acid
methylmalonic acid
dimethylmalonic acid
ethylmalonic acid
propylmalonic acid
diethylmalonic acid
butylmalonic acid
(2-cyclopentene-1-yl)malonic acid
phenylmalonic acid
benzylmalonic acid
methylsuccinic acid
methylene succinic acid
(itaconic acid)
1-octadecenylsuccinic acid
2,2dimethylsuccinic acid
2,3dimethylsuccinic acid
2-methylglutaric acid
3-methylglutaric acid
2,2-dimethylglutaric acid 3,3-dimethylglutarlc acid
2,4-dimethylglutaric acid
2,3-dimethylglutanic acid
2,3-dimethmaleic acid (cis)
2,3-dimethylfumaric acid (trans)
methylmaleic acid
(citraconic acid)
methylfumaric acid
(mesaconic acid)
phenylmaleic acid
cyclohexane-1,4-dicarboxylic acid
4-methylhexahydrophthalic acid
1,1-cyclohexanediacetic acid
cis/trans-4-cyclohexene-1,2-dicarboxylic acid
exo/endo-5-norbornene-2,3-dicarboxylic acid
methyl-5-norbornene-2,3-dicarboxylic acid
exo-7-oxabicyclo[2.2.1]hept-5-ene-2,3-dicarboxylic acid
=exo-3,6-epoxy-1,2,3,6-tetrahydrophthalic acid
1,3-adamantanediacetic acid
phthalic acid
isophthalic acid
terephthalic acid
4-methylphthalic acid
2-methoxyisophthalic acid
5-methylisophthalic acid
5-tert.butylisophthalic acid
3-phenylglutaric acid
TCD-carboxylic acid DS =
tricycio[5.2.1.0$^{2,6}$]decane-3(4),8(9)-dicarboxylic acid
8,8'-di(tricyclo[5.5.1.0$^{2,6}$]decyl)ether-3(4),3'(4')-dicarboxylic acid
tetramethylterephthalic acid
o,m,p-phenylenedioic acetic acid
o,m,p-phenylenedioxydioic acetic acid

TABLE VI-continued

Carboxylic Acid for the Synthesis of TCD - Esters (oxadiethanoic acid)
DL-tartaric acid 2,2'-thiodiacetic acid
(thiodiglycolic acid)
3,3'-thiodipropionic acid
3,3'-dithiodipropionic acid
cyclopropane-1,1-dicarboxylic acid
cyclobutane-1,1-dicarboxylic acid
cyclobutane-1,2-dicarboxylic acid
3,3[tetramethyleneglutaric acid
cyclopentane-1,2-dicarboxylic acid
camphoric acid
cyclohexane-1,2-dicarboxylic acid
cyclohexane-1,3-dicarboxylic acid o,m,p-carboxyphenoxyacetic acid
p-phenylenedipropionic acid
2,5-dihydroxybenzol-1,4-diacetic acid
diphenyldisulfid-2,2'-dicarboxylic acid
(2,2'-dithiosalicylic acid)
diphenylcarboxylic acid
1,5-decalindicarboxylic acid
(5-dihydroxydecahydronaphthalene)
1,8-naphthalic acid
(naphthalene-1,8-dicarboxylic acid)
2,3-naphthalene-dicarboxylic acid
1,4-naphthalene-dicarboxylic acid
2,6-naphthalene-dicarboxylic acid
1,5-naphthalene-dicarboxylic acid Tricarboxylic Acids:

1,2,3-propane tricarboxylic acid
(tricarballylic acid)
2-methyl-1,2,3-propanetricarboxylic acid
(α-methyl-tricarboxylic acid)
1,3,5-pentane tricarboxylic acid
1,2,3-propenetricarboxylic acid
(aconitic acid)

citric acid
1,2,4-benzoltricarboxylic acid
(trimellitic acid)
1,3,5-benzoltricarboxylic acid
(trimesitic acid)

TABLE VII

Alcohols for the Synthesis of TCD - Esters and/or Ethers

Mono - Alcohols:
methanol
ethanol
n/iso-propanol
n/iso-butanol
sec-butyl alcohol
tert-butyl alcohol
1-pentanol
1-hexanol
1-heptanol
1-octanol
1-nonanol
1-decanol
2-methyl-2-hexanol
1-undecanol
1-dodecanol
2-methyl-1-butanol
2,2-dimethyl-1-propanol
(neopentylalcohol)
2-methyl-1-propanol
3-methyl-1-butanol
2,2-dimethyl-1-butanol
3,3-dimethyl-1-butanol
2-ethyl-1-butanol
3-methyl-1-pentanol
4-methyl-1-pentanoi
2,2-dimethyl-1-pentanol
2,3-dimethyl-1-pentanol
2-ethylhexanol
2-ethyl-2-propylhexanol
2-pentanol
3-pentanol
2-hexanol
3-hexanol
2-heptanol
3-heptanol
4-heptanol
2-octanol
2,3-dimethyl-4-pentene-2-ol
2-hexene-1-ol
4,4-dimethyl-2-methylene-1-pentanol
2-ethyl-2-hexene-1-ol
4-hexene-3-ol
1-hexene-3-ol
5-hexene-3-ol 3-octanol
4-octanol
2-nonanol
3-nonanol
4-nonanol
5-nonanol
2-decanol
3-decanol
4-decanol
5-decanol
2-methyl-2-butanol
(tert. amylic alcohol)

3-methyl-2-butanol
3,3-dimethyl-2-butanol
2,3-dimethyl-2-butanol
3-methyl-2-pentanol
4-methyl-2-pentanol
3-ethyl-2-pentanol
2-methyl-3-pentanol
2,2-dimethyl-3-pentanol
2,4-dimethyl-3-pentanol
3-methyl-2-hexanol
2-methyl-3-hexanol
5-methyl-3-hexanol
4-ethyl-3-hexanol
3,4-dimethyl-2-hexanol
2,2-dimethyl-3-hexanol
2,5-dimethyl-3-hexanol
6-methyl-2-heptanol
S-ethyl-2-heptanol
4-methyf-3-heptanol
S-methyl-3-heptanol
3-methyl-4-heptanol
2,2-dimethyl-3-heptanol
2,4-dimethyl-3-heptanoI
2-methyl-3-octanol
cyclo octanemethanol
cyclo undecanemethanol
cyclo dodecanemethanol
2-norbornanemethanol
3-methylnorbornane-2-methanol
1-adamantanemethanol
6,6-dimethylbicyclo[3.1.1]hept-2-ene-2-ethanol 3-methyl-4-octanol
4-methyl-3-nonanol
2-methyl-3-nonanol
2-methyl-4-nonanol
3-methyl-4-nonanol
2-methyl-2-pentanol
3-methyl-3-pentanol
3-ethyl-3-pentanol
2,4-dimethyl-2-pentanol
2,3-dimethyl-3-pentanol
2,2,4-tnmethyl-3-pentanol 3-methyl-3-hexanol
2,3-dimethyl-3-hexanol
2,5-dimethyl-2-hexanol
3,4-dimethyl-3-hexanol
3,5-dimethyl-3-hexanol
2-methyl-2-heptanol
3-methyl-3-heptanol
3-ethyl-3-heptanol
4-methyl-4-heptanol
4-methyl-4-octanol
4-methyl-4-nonanol
3,5,5-trimethylhexanol
(isononylic aicohol
crotylic alcohol
3-methyl-2-butene-1-ol
3-butene-1-ol
2-methyl-3-butene-2-ol
4-pentene-1-ol
4-pentene-2-ol
1-pentene-3-ol
3-pentene-2-ol
4-methyl-3-pentene-2-ol
4-methyl-1-pentene-3-ol
2-methyl-4-pentene-2-ol

TABLE VII-continued

Alcohols for the Synthesis of TCD - Esters and/or Ethers 3-ethyl-5-hexene-3-ol
3,5-dimethyl-5-hexene-3-ol
3-heptene-1-ol
1-heptene-3-ol
2-heptene-4-ol
2-methyl-1-heptene-3-ol
4-methyl-1-heptene-4-ol
1-octene-3-ol
1-octene-4-ol
3,7-dimethyl-6-octene-l-ol
(citronellol)
cyclo butane-1-ol
cyclopropylmethylcarbinol
dicyclopropylcarbinol
cyclobutanol
cyclopentanol
cyclohexanol
cycloheptanol
cyclooctanol
cyclopentylmethanol
2-cyclopentylethanol
1 cyclopentylethanol
3-cyclopentyl-1-propanol
cyclohexylmethanol
2-methylcyclopentanol
1-cyclohexylethanol
1-cyclohexyl-1-propanol
1-cyclohexyl-1-butanol 2-cyclohexylethanol
3-cyclohexene-1-methanol
3-cyclohexene-1-ethanol
cycloheptanemethanol
TCD-alcohol A
= 5-hydroxy-tricyclo [5.2.1.0$^{2,6}$]decane
3(4)-hydroxy4ricyclo[5.2.1.026]decane
TCD-alcohol M
= 8-hydroxymethylcyclo[5.2.1.0$^{2,6}$]decane
3(4)-hydroxymethyl-tricyclo[5.2.1.0$^{2,6}$]decane
TCD alcohol E
= 8(9)-hydroxy-tricyclo[5.2.1.0$^{2,6}$]dec-3-ene
5-hydroxy-tricyclo[5.2.1.0$^{2,6]dec-3-ene}$
1-adamantanol
2-adamantanol
decahydro-1 (2)-naphthol
di-2-norbornylmethanol
2-methoxyethanol
2-ethoxyethanol
2-propoxyethanol
2-butoxyethanol
3-ethoxy-1-propanol
3-methoxy-1-butanol
2-isopropyloxyethanol
1 ,3-diethoxy-2-propanol
diethyleneglycolmonomethylether
(methyldiglycol)
diethyleneglycolmonoethylether
(ethyldiglycol)
diethyteneglycolmonobutylether
(butyldiglycol)
4-ethoxy-1-decalol
3-hydroxytetrahydrofurane
tetrahydroxyfurfurylalcohol
tetrahydropyrane-2-methanol
2,2-dimethyl-1,3-dioxolane
(solketal)
diacetonealcohol
benzylalcohol
α-methytbenzylalcohol
α,α-dimethylbenzylatcohol
α-ethylbenzytalcohol
1-phenyl-1-butanol
2-hydroxymethyl-1 ,4-benzodioxane
1(2)-naphthalenemethanol
9-fluorenemethanol
1-fluorenemethanol (napol)

1-methyl cyclopentanol
1-ethyl cyclopentanol
1-(n-propyl)-1-cyclopentanol
1-(n-butyl)-1-cyclopentanol
2-cyclohexene-1-ol
1 -methylcyclohexanol
2-methylcyclohexanol
2-ethylcycIohexanol
3-methylcyclohexanol
4-methylcyclohexanol
4-ethylcyclohexanol
4-tert. butylcyclohexanol
2,3-dimethylcyclohexanol
2,5-dimethylcyclohexanol
2,4-dimethylcyclohexanol
2,6-dimethylcyclohexanol
3,5-dimethylcycIohexanol
3,4-dimethylcycIohexanol
3,3,,5-trimethylcyclohexanol
dl-menthol
p-menth-1-ene-9-ol
isopulegol
bornyl alcohol, isoborneol
myrtanol
1-methylcyclooctanol
cyclododecanol
norborneol
(endo/exo)

5-norbornene-2-ol
borneol 1-phenyl-1-pentanol
cyclopropylphenylcarbinol
1 cyclopropyl--methylbenzylalcohol
cyclohexylphenylcarbinol
1-phenyl-1-cyclohexanol
2-phenyl-1-cyclohexanol
benzhyd rol
1,1-dlphenylethanol
α-benzylbenzhydrol
o-phenyethylbenzylalcohol
2-methoxybenzylalcohol
3-methoxybenzylalcohol
4-menthoxybenzylalcohol
4-methylbenzylalcohol
p-tert. butylbenzylatcohol
p-butoxybenzylalcohol
p-dimethylbenzytalcohol
p-methyl-α-(n-propyl)benzylalcohol
4,4'-dimethoxybenzylalcohol
o-phenoxybenzylalcohol
p-methoxy-α-methylbenzylalcohot
p-methoxy-α-ethylbenzylalcohol
α-cyclopropyt-p-methylbenzylalcohol
(cyclopropyl-p-toluic carbinol)
α-cyclopropyl-α,p-dimethytbenzylalcohol
α-cyctopropyl-p-methoxybenzylalcohol
2,3-dimethoxybenzylalcohol
2,4-dimethoxybenzylalcohol
3,4-dimethoxybenzylalcohol
3,5-dimethoxybenzylalcohol
3,4-methylenedioxyphenylmethanol
(Piperonylic alcohol)
3,4,5-trimethoxybenzylalcohol
4-biphenylmethanol
(p-phenylbenzylalcohol)
m(p)-benzyloxybenzylalcohot
1,2,3,4-tetrahydro-1-naphthot
benzo-2,3-dihydroxypyrane-4-ot
(4-chromanol)
2-phenyl-1-propanol
β-ethylphenethylalcohol
3-phenyl-1-propanol
3,3-diphenyl-i-propanol TABLE VII-continued Alcohols for the Synthesis of TCD - Esters and/or Ethers

| | |
|---|---|
| 9-hydroxyfluorene | benzyl-tert. butanol |
| 1-acenaphthenol | 2-phenoxyethanol |
| dibenzosuberol | 1-naphthalinethanol |
| 9-anthracenemethanol | 1(o-benzylphenoxy)-2-propanol |
| phenethylalcohol | |
| Dialcohols (Dioles) | |
| ethylenegycol | 1,12-dodecanediol |
| 1,2-propanediol | cyclohexane-1,1-dimethanol |
| 1,3-propanediol | 3-cyclohexene-1,1-dimethanol |
| 2,2-dimethyl-1,3-propanediol | 1,5-cyclooctanediol |
| (neopentylglycol) | 2,2,4,4-tetramethyl-1,3-cyclobutanediol |
| 2,2-diethyl-1,3-propanediol | 1,2-cyclohexanediol |
| 2-ethyl-2-methyl-1,3-propanediol | 1,3-cyclohexanediol |
| 2-methyl-2-propyl-1,3-propanediol | 1,4-cyclohexanediol |
| 2-n-butyl-2-ethyl-1,3-propanediol | 1,2-cycloheptanediol |
| 1,4-butenediol | 1,2-cyclododecanediol |
| 2-methyl-1,4-butanediol | 1,4-decalenediol |
| 1,3-butanediol | 1,5-decalenediol |
| 1,2-butanediol | TCD-alcohol DM |
| 2,3-butanediol | = 3(4),B(9)-bis(hydroxymethyl)tricyclo[5.2.1.0 $^2$ ]decane |
| pinacol | 3(4),8(9)-bis(hydroxymethyl)tricyclo[5.2.1.0 $^{2,6}$ ]decane |
| (1,3-dimethyl-2,3-butanediol) | TCD-alcohol OM |
| 1,5-pentanediol | 8-hydroxy-4(5)hydroxymethyl4ncyclo[5.2.1.0 $^{2,6}$ ]decane |
| 2,4-pentanediol | 3,4-dihydroxytricyclo[5.2.1.0 $^{2,6}$ ]decane |
| 2-methyl-2,4-pentanediol | di-TCD-alcohol M)ether |
| 1,6-hexanediol | = di(tricyclo[5.2.1.0 $^{2,6}$ ]decyl-8,8'-ether-3(4))dimethylol |
| 2,5-hexanediol | di-TCD-alcohol A)ether |
| 2-ethyl-1,3-hexanediol | = di (tricyclo[5.2.1.0 $^{2,6}$ ]decyl-8,8'-ether-3(4),3'(4'))diol |
| 2,5-dimethyl-2,5-hexanediol | 5,9-cyclododecanedien-1,2-diol |
| 1,7-heptanediol | 2-butene-1,4-diol |
| 1,8-octanediol | 3-hexene-2,5-diol |
| 1,9-nonanediol | 1,2-cyclobutanedimethanol |
| 1,10-decanediol | 1,4-cyclohexanedimethanol |
| 5-norbornene-2,2-dimethanol | 4(2-hydroxyethoxy)-1-decatol |
| diethyleneglycol | 2,4-dihydro-2H-pyrane-2,2-dimethanol |
| triethyleneglycol | 1,2-benzoldimethanol |
| tetraethyleneglycol | 1,3-benzoldimethanol |
| polyethyleneglycol | 1,4-benzoldimethanol |
| dipropyleneglycol | tetramethyl-p-xylol--,&-diol |
| polypropyleneglycol | 2,2-diphenyl-1,3-propanediol |
| polyletrahydrofurane | 1-phenyl-1,2-ethanediol |
| (poly- 1,4-butanediol) | (styreneolycol) |
| Polvalcohols (Polvoles) | |
| glycerol | pentaerylhrite |
| trimethylolethane | dipentaerylhrite |
| trimethylolpropane | meso-erylhritol |
| 2-hydroxymethyl-2propyl-1,3propanediol | TCD-atcohol TO |
| 1,2,6-trihydroxyhexane | = 8(9),3(4)-tri-hydroxy-tricyclo[5.2.1.0 $^{2,6}$ ]decane |
| 2,5-dimethyl-1,2,6-hexanetriol | 8-hydroxy-4,4-dihydroxymethyl-tricycto[5.2.1.0 $^{2,6}$ ]decane |

What is claimed is:

1. An immersion oil for microscopy, the immersion oil comprising:

as a main constituent, the tricyclodecane derivative or derivatives of substances having the basic structure of the tricyclodecane;

said tricyclodecane derivative or derivatives being esters or ethers of tricyclodecanes or said tricyclodecane derivatives being esters or ethers of substances having base structures of tricyclodecanes; and, said immersion oil further including minor constituents comprising one or more high-boiling liquids.

2. The immersion oil of claim 1, wherein said substances are tricyclodecanepolymers or tricyclodecaneoligomers.

3. The immersion oil of claim 1, wherein the main constituent is selected from the group consisting of tricyclodecane-methylolesters and tricyclodecanemethylolethers.

4. The immersion oil of claim 1, wherein said immersion oil further comprises minor constituents comprising one or more high-boiling liquids.

5. The immersion oil of claim 4, wherein the high-boiling liquids are selected from the group consisting of paraffin oil, softeners, polypropylglycol, butylbenzylphthalate, dioctylphthalate, dioctylsebacate and di-(propyleneglycol-1.2)dibenzoate.

6. The immersion oil of claim 1, wherein the portion of the tricyclodecane derivative or the derivative of substances having the base structure of the tricyclodecane is greater than 50% by weight.

7. The immersion oil of claim 1, wherein the portion of the tricyclodecane derivative or the derivative of substances having the base structure of the tricyclodecane is greater than 60% by weight.

8. Di-(tricyclodecanemethylol)adipate produced by esterification of 8(9)-hydroxymethyltricyclo [5.2.1.0 $^{2,6}$ ] decane and adipic acid followed by vacuum distillation of the esters obtained.

9. An immersion oil for microscopy, the immersion oil comprising:

as a main constituent, the tricyclodecane derivative or derivatives of substances having the basic structure of the tricyclodecane; and, said main constituent being selected from the group consisting of: di-(tricyclodecane methylol)adipate, di-(tricyclodecane methylol)phthalate, di-(tricyclodecane methylol)malonate, di-(tricyclodecanemethylol) succinate, di-(tricyclodecane methylol)maleinate, di-(tricyclodecanemethylol)glutarate and di-(tricyclodecanemethylol)sebacate.

10. The immersion oil of claim 9, wherein said immersion oil further comprises minor constituents comprising one or more high-boiling liquids.

11. The immersion oil of claim 10, wherein the high-boiling liquids are selected from the group consisting of paraffin oil, softeners, polypropylglycol, butylbenzylphthalate, dioctylphthalate, dioctylsebacate and di-(propyleneglycol-1.2)dibenzoate.

12. The immersion oil of claim 9, wherein the portion of the tricyclodecane derivative or the derivative of substances having the base structure of the tricyclodecane is greater than 50% by weight.

13. The immersion oil of claim 9, wherein the portion of the tricyclodecane derivative or the derivative of substances having the base structure of the tricyclodecane is greater than 60% by weight.

14. Di-(tricyclodecanemethylol)adipate having the formula:

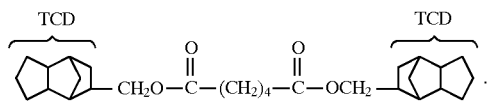

15. An immersion oil for microscopy, the immersion oil comprising:

as a main constituent, di-(tricyclodecanemethylol)ester or di-(tricyclodecanemethylol)ether or substances having the basic structure of di-(tricyclodecanemethylol)esters or di-(tricyclodecanemethylol)ethers.

16. The immersion oil of claim 15, wherein the main constituent is selected from the group consisting of: di-(tricyclodecane methylol)adipate, di-(tricyclodecane methylol)phthalate, di-(tricyclodecane methylol)malonate, di-(tricyclodecanemethylol)succinate, di-(tricyclodecane methylol)maleinate, di-(tricyclodecanemethylol)glutarate and di-(tricyclodecanemethylol)sebacate.

17. The immersion oil of claim 15, wherein said immersion oil further comprises minor constituents comprising one or more high-boiling liquids.

18. The immersion oil of claim 17, wherein the high-boiling liquids are selected from the group consisting of paraffin oil, softeners, polypropylglycol, butylbenzylphthalate, dioctylphthalate, dioctylsebacate and di-(propyleneglycol-1.2)dibenzoate.

19. The immersion oil of claim 15, wherein the portion of the di-(tricyclodecanemethylol) ester or ether or substances having the basic structure of di-(tricyclodecanemethylol) esters or ethers is greater than 50% by weight.

20. The immersion oil of claim 15, wherein the portion of the di-(tricyclodecanemethylol) ester or ether or substances having the basic structure of di-(tricyclodecanemethylol) esters or ethers is greater than 60% by weight.

* * * * *

UNITED STATES PATENT AND TRADEMARK OFFICE
CERTIFICATE OF CORRECTION

PATENT NO.    : 5,817,256
DATED         : October 6, 1998
INVENTOR(S)   : Hans-Joachim Weippert It is certified that error appears in the above-identified patent and that said Letters Patent is hereby corrected as shown below:

Column 1,
Line 26, delete "$V_e$" and substitute -- $\upsilon_e$ -- therefor.

Column 2,
Lines 31 and 32, delete "8 (9) -dihydroxymethyltricyclo|5.2.1.0$^{2,6}$]decane)" substitute
-- 8 (9) -dihydroxymethyltricyclo|5.2.1.0$^{2,6}$]decane) -- therefor.

Column 3,
Line 34, delete line 34.

Column 4,
Line 1, delete "$v_e$" (all occurrences) and substitute -- $\upsilon_e$ -- therefor.
Line 2, delete "$v_e$" and substitute -- $\upsilon_e$ -- therefor.
Table Ia, column 1, line 8, delete "Di-(TCDmethylol) suoccinate" and substitute
-- Di-(TCDmethylol) succinate -- therefor.
Table Ia, column 1, line 11, delete "Di-(TCDmethylol) sebaoate" and substitute
-- Di-(TCDmethylol) sebacate -- therefor.

Column 5,
Table Ia, column 1, line 4, delete "Di-(TCDmethylol) succinate" and substitute
-- Di-(TCDmethylol) succinate -- therefor.
Table Ia, column 1, line 11, delete "Di-(TCDmethylol) sebaoate" and substitute
-- Di-(TCDmethylol) sebacate -- therefor.
Table Ia, column 2, in the last line, move the text in column 2 to column 3.
Table II, column 2, line 1, delete "7.0" and substitute -- 70 -- therefor.

Column 7, Table III,
Line 2, delete "$C_2H_5$" and substitute -- -$C_2H_5$ -- therefor.

Column 11, Table IV,
Under TCD-(Mono)alcohols, delete "TCD-Alcohol =" and substitute -- TCD-Alcohol A
= -- therefor.

Column 13, Table IV,
Under TCD - tri-Alcohols, delete "III." and substitute -- XIII. -- therefor.

Column 15, Table V,
Delete , TCD-Dicarboxylic Acids:".
Above "XX.", insert -- TCD-Dicarboxylic Acids: --.

UNITED STATES PATENT AND TRADEMARK OFFICE
CERTIFICATE OF CORRECTION

PATENT NO. : 5,817,256
DATED : October 6, 1998
INVENTOR(S) : Hans-Joachim Weippert It is certified that error appears in the above-identified patent and that said Letters Patent is hereby corrected as shown below:

Column 17,
Line 2, between "äther" and "4,4'", insert a hyphen.
Line 4, between "äther" and "4,4'", insert a hyphen.

Column 18, Table VI, column 2,
Line 22, delete "cyctohexyl" and substitute --cyclohexyl -- therefor.

Column 19, Table VI, column 2,
Line 8, delete "cyciopentane" and substitute -- cycloipentane -- therefor.

Column 19, Table VI, column 1,
Line 13, delete "(3,4-dimethQxyphenyl) acetic" and substitute therefor
-- (3, 4-dimethoxyphenyl) acetic --.
Line 22, delete "2,342,6/3,4/2,4/2,5-dimethoxybenzoic" and substitute therefor
-- 2,3-/2,6/3,4/2,4/2,5-dimethoxybenzoic --.
Line 26, delete "cyciohexyloxybenzoic" and substitue -- cyclohexyloxybenzoic -- therefor.
Line 45, delete "(toxii" and substitute -- (toxil -- therefor.

Column 19, Table VI, column 2,
Line 71, delete "tricycio [5.2.1.60$^{2,6}$]decane-3(4), 8 (9) -dicarboxylic" and substitute
-- tricyclo [5.2.1.0$^{2,6}$]decane-3 (4),8(9) -dicarboxylic -- therefor.

Column 21, Table VI, column 1,
Line 12, delete "3,3 [tetramethyleneglutaric" and substitute therefor
-- 3,3-tetramethyleneglutaric --.
Line 21, delete "(α-methyl-tricarboxylic" and substitute therefor -- (β-methyl-tricarboxylic --.

Column 21, Table VI, column 2,
Line 12, delete "2,3-napthaiene-dicarboxylic" and substitute therefor -- 2,3-napthalene-dicarboxylic --.

Column 21, Table VII, column 1,
Line 15, move the text in column 1 to column 3.

Column 21, Table VII, column 1,
Line 27, delete "4-methyl-l-pentanoi" and substitute -- 4-methyl-1-pentanol -- therefor.

UNITED STATES PATENT AND TRADEMARK OFFICE
CERTIFICATE OF CORRECTION

PATENT NO. : 5,817,256
DATED : October 6, 1998
INVENTOR(S) : Hans-Joachim Weippert It is certified that error appears in the above-identified patent and that said Letters Patent is hereby corrected as shown below:

Column 21, Table VII, column 2,
Line 33, delete "S-ethyl-2-heptanol" and substitute -- 5-ethyl-2-heptanol -- therefor.
Line 34, delete "4-methyf-3-heptanol" and substitute -- 4-methyl-3-heptanol -- therefor.
Line 35, delete "S-methyl-3-heptanol" and substitute -- 5-methyl-3-heptanol -- therefor.

Column 23, Table VII, column 1,
Line 37, delete "5-hydroxy-tricyclo [5.2.1.0$^{2,6}$] decane" and substitute therefor -- 8-hydroxy-tricyclo [5.2.1.0$^{2,6}$] decane --.
Line 38, delete "3(4) -hydroxy4ricyclo [5.2.1.026] decane" and substitute therefor -- 3(4)-hydroxy-tricyclo [5.2.1.0$^{26}$] decane --.
Line 44, delete "5-hydroxy-tricyclo [5.2.1.0$^{2,6}$] $^{dec-3-ene}$" and substitute therefor -- 5-hydroxy-tricyclo [5.2.1.0$^{2,6}$] dec-3-ene --.
Line 71, delete "α-methytlbenzylalcohol" and substitute therefor -- α-methylbenzylalcohol --.

Column 23, Table VII, column 2,
Line 23, delete "1 cyclopropyl-methylbenzylalcohol" and substitute therefor -- α-cyclopropyl-α-methylbenzylalcohol --.
Line 42, delete "benzhyd rol" and substitute -- benzhydrol -- therefor.
Line 52, delete "p-dimethylbenzytalcohol" and substitute therefor -- p-dimethylbenzylalcohol --.
Line 58, delete "α-cyclopropyt-p-methylbenzylalcohol" and substute therefor -- α-cyclopropyl-p-methylbenzylalcohol --.
Line 71, delete "m(p) -benzyloxybenzylalcohot" and substitute therefor -- m (p) -benzyloxybenzylalcohol --.
Line 72, delete "1, 2, 3, 4-tetrahydro-1-naphthot" and substitute therefor -- 1, 2, 3 ,4-tetrahydro-1-naphthol --.
Line 73, delete "benzo-2, 3-dihydroxypyrane-4-ot" and substitute therefor -- benzo-2, 3-dihydroxypyrane-4-ol --.
Line 78, delete "3, 3-diphenyl-i-propanol" and substitute therefor -- 3, 3-diphenyl-1-propanol --.

Column 25, Table VII, column 1,
Line 6, delete "Dialcohols (Dioles)" and substitute -- Dialcohols (Dioles) -- therefor.
Line 42, delete "polyletrahydrofurane" and substitute -- polytetrahydrofurane -- therefor.
Line 44, delete "Polvalcohols (Polvols)" and substitute therefor -- Polyalcohols (Polyols) --.

UNITED STATES PATENT AND TRADEMARK OFFICE
CERTIFICATE OF CORRECTION

PATENT NO. : 5,817,256
DATED : October 6, 1998
INVENTOR(S) : Hans-Joachim Weippert It is certified that error appears in the above-identified patent and that said Letters Patent is hereby corrected as shown below:

Column 25, Table VII, column 2,
Line 20, delete "= 3(4), B(9) -bis(hydroxymethyl) tricyclo [5.2.1.02] decane" and substitute therefor -- = 3 (4), 8(9)-bis(hydroxymethyl) tricyclo [5.2.1.0$^{2,6}$] decane --.
Line 23, "8-hydroxy-4 (5) hydroxymethy14ncyclo [5.2.1.0$^{2,6}$] decane" and substitute therefor -- 8-hydroxy-4 (5) hydroxymethyl-tricyclo [5.2.1.0$^{2,6}$] decane --.
Line 24, delete "3,4-dihydroxytricyclo [5.2.1.0$^{2,6}$] decane" and substitute therefor -- 3,4-dihydroxy-tricyclo [5.2.1.0$^{2,6}$] decane --.
Line 25, delete "di-TCD-alcohol M) ether" and substitute therefor -- di (TCD-alcohol M) ether --.
Line 27, delete "di-TCD-alcohol A) ether" and substitute therefor -- di (TCD-alcohol A) ether --.
Line 35, delete "-decatol" and substitute -- decalol -- therefor.
Line 40, delete "tetramethyl-p-xylol,&-diol" and substitute therefor -- "tetramethyl-p-xylol-α,α'-diol --.
Line 43, delete "styreneolycol" and substitute -- styreneglycol -- therefor.
Line 45, delete "pentaerylhrite" and substitute -- pentaerythrite -- therefor.
Line 46, delete "dipentaerylhrite" and substitute -- dipentaerythrite -- therefor.
Line 47, delete "meso-erylhriol" and substitute -- meso-erythritol -- therefor.
Line 48, delete "TCD-atcohol" and substitute -- TCD-alcohol -- therefor.
Line 50, delete "8-hydroxy-4, 4-dihydroxymethyl-tricycto [5.2.1.0$^{2,6}$] decane" and substitute therefor -- 8-hydroxy-4, 4-dihydroxymethyl-tricyclo [5.2.1.0$^{2,6}$] decane --.

Signed and Sealed this

Eleventh Day of December, 2001

*Attest:*

*Attesting Officer*

NICHOLAS P. GODICI
*Acting Director of the United States Patent and Trademark Office*